United States Patent [19]

Lambert et al.

[11] Patent Number: 4,931,456
[45] Date of Patent: Jun. 5, 1990

[54] FUNGICIDAL OXIME NICOTINATES

[75] Inventors: Claude Lambert, Lyons; Regis Pepin, Rilleux La Pape; Marie-Pascale Latorse, Lyons, all of France

[73] Assignee: Rhone-Poulenc Agrochimie, Lyons, France

[21] Appl. No.: 270,020

[22] Filed: Nov. 14, 1988

[30] Foreign Application Priority Data

Nov. 12, 1987 [FR] France ................................ 87 15897

[51] Int. Cl.$^5$ ................. C07D 213/57; C07D 213/55; C07D 401/12; A01N 43/40
[52] U.S. Cl. ..................................... 514/318; 514/343; 514/350; 546/286; 546/288; 546/263; 546/281; 546/193; 546/194
[58] Field of Search ............... 546/286, 288, 263, 281, 546/193, 194; 514/350, 318, 343

[56] References Cited

U.S. PATENT DOCUMENTS 4,244,959 1/1981 Freenor ............................... 514/357

Primary Examiner—Alan L. Rotman
Attorney, Agent, or Firm—Burns, Doane, Swecker & Mathis

[57] ABSTRACT

Nicotinic derivatives. They have the formula:

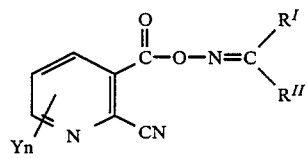

with $R^1$, $R^2$, which are identical or different, =H, alkyl ($C_1$-$C_{18}$) optionally substituted phenyl, pyridyl; Y=H, hal, alkyl or alkoxy or $C_1$-$C_4$; n=integer from 1 to 3.

Agricultural fungal compounds.

4 Claims, No Drawings

FUNGICIDAL OXIME NICOTINATES

The present invention relates to fungicidal compositions based on nicotinic derivatives, to new nicotinic derivatives and to the use of nicotinic derivatives for combating fungal diseases of plants.

The invention relates more particularly to fungicidal compositions which contain as active material at least one compound of formula:

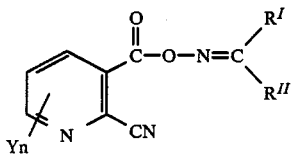

in which:
—$R^I$ or $R^{II}$ which are identical or different, are
a hydrogen atom,
a linear or branched alkyl radical containing from 1 to 18, and preferably from 1 to 4, carbon atoms;
or form, with the carbon atom bonded to the nitrogen atom, a 5- or 6-membered ring, itself capable of carrying a phenylydene, through the intermediacy of two adjacent carbon atoms;
a phenyl radical substituted, if desired, by at least one substituent chosen from the group comprising a halogen atom, an alkyl containing from 1 to 4 carbon atoms, an alkoxy containing from 1 to 4 carbon atoms, an amino substituted, if desired, by at least one alkyl containing from 1 to 4 carbon atoms, a nitro, another dioxyalkylene ($C_1$-$C_3$) carried by two adjacent phenyl carbon atoms, a pyridyl radical;
—Y is a hydrogen or halogen atom, or an alkyl or alkoxy radical containing from 1 to 4 carbon atoms; and
—n is an integer from 1 to 3, or one of its isomers.

The compounds according to the invention may be prepared by reaction of a compound of formula II with a chlorinating agent to give an acyl chloride derivative III which is reacted with an oxime, according to the scheme (Process III B):

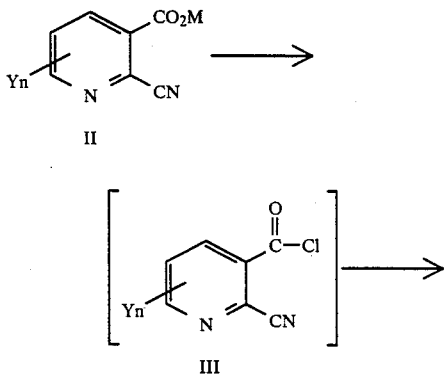

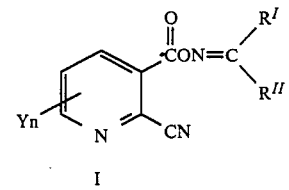

I in which M is an alkali metal atom.

The treatment of II with a chlorinating agent, such as phosgene, oxalyl chloride or thionyl chloride, in an aliphatic solvent such as a chloroalkane, yields the derivative III. The latter is converted into compound I by reaction with the appropriate oxime in the presence of an organic base such as, for example, pyridine.

The following examples illustrate the preparation of the compounds according to the invention and their fungicidal properties. The structure of these compounds has been verified by NMR spectrography.

EXAMPLE 1

Acetone O-[(2-cyano-3-pyridylcarbonyl)oxime [compound no. 1)

Oxalyl chloride (2.8 g, 0.022 mole) is added dropwise to a suspension of potassium 2-cyanonicotinate (4.1 g, 0.022 mole) in dichloromethane (40 ml). The mixture is then heated under reflux for one hour. A solution of acetone oxime (1.46 g, 0.02 mole) and pyridine (1.6 g, 0.02 mole) in dichloromethane (10 ml) is then added to the mixture, at 20° C. The mixture is then stirred for 2 hours at 20° C., is washed with water and then dried over $Na_2SO_4$. After evaporation of the solvent and recrystallization from pentane, a yellow solid (3.4 g, 83%) corresponding to the above structure is obtained (mp: 92° C.).

EXAMPLE 2

4-Chlorobenzaldehyde O-(2-cyano-3-pyridylcarbonyl)oxime (compound no. 2)

Oxalyl chloride (2.8 g, 0.022 mole) is added dropwise to a suspension of potassium 2-cyanonicotinate (4.1 g, 0.022 mole) in dichloromethane (40 ml). The mixture is then heated under reflux for one hour. A solution of 4-chlorobenzaldehyde oxime (3.1 g, 0.02 mole) and pyridine (1.6 g, 0.02 mole) in dichloromethane (20 ml) is then added to the mixture, at 20° C. The mixture is then stirred for 2 hours at 20° C. The solvent is evaporated off and the residue treated with water (50 ml). The solid formed is filtered off and is washed with water and then with ethyl ether. A white solid 4.4 g, 77%) corresponding to the structure 2 is thus obtained (M.p.: 160° C.).

EXAMPLES 3 TO 5

By operating according to either of the two receding Examples, the following compounds are obtained, hose structures and physiochemical characteristics are collated in the following table:

Structure:

[Pyridine ring with N, CN substituent, and C(=O)-O-N=C(R^I)(R^II) group]

| Compound No. | R^I | R^II | Melting Point (°C.) |
|---|---|---|---|
| 1 | CH₃ | CH₃ | 92 |
| 2 | H | 4-Cl-phenyl | 160 |
| 3 | H | 2-Cl-phenyl | 159 |
| 4 | H | 3,4-diCl-phenyl | 161 |
| 5 | H | 4-Br-phenyl | 93 |
| 6 | H | 4-OCH₃-phenyl | 134 |
| 7 | H | 3,4-diOCH₃-phenyl | 152 |
| 8 | H | 3,4-methylenedioxy-methyl phenyl | 142 |
| 9 | H | pyridyl | 157 |

EXAMPLE 10

Greenhouse test, on Piricularia oryzae

Rice plants (Rosa Marchetti variety) 10 cm in height, grouped in small troughs of 2, are treated by watering the soil, with an aqueous suspension containing:
30 mg of the product to be tested
15 mg of a surface-active agent, a condensate of ethylene oxide (20 moles) with sorbitan monooleate
water q.s. 30 ml.

This suspension, applied to square pots with a side of 7 cm, corresponds to a dosage of approximately 60 kg/ha of active substance. The product is left to be absorbed by the soil. A proportion of the rice plants has not been treated, in order to act as controls. After 24 hours following the treatment all the rice plants are contaminated with a suspension of spores of *Piricularia oryzae*, obtained by scratching an in vitro culture, by spraying onto the foliage at a rate of 5 ml of suspension per pot. The pots are left to incubate for 24 h at 25° C. at 100° C. of relative humidity. The plants are then transferred to an observation cell.

The observation is carried out 7 days following the contamination.

Under these conditions it is noted that an inhibition of at least 80% of the fungus is obtained with the compounds 1, 2, 8 and 9 in a dosage of 60 kg/ha.

These experiments show well the systemic fungicidal properties of the compounds according to the invention and their remarkable action on the piriculariosis of rice.

These compositions may also contain all kinds of other ingredients such as, for example, protective colloids, adhesives, thickeners, thixotropic agents, penetrating agents, stabilizers, sequestrants, and the like, as well as other known active substances with pesticidal properties (especially insecticides or fungicides) or with properties promoting plant growth (especially fertilizers) or with plant growth-regulating properties. More generally, the compounds according to the invention may be combined with any solid or liquid additives corresponding to the usual formulation methods.

In the case of a use of the compounds according to the invention as fungicides, these use dosages may vary within wide limits, especially depending on the virulence of the fungi and the climatic conditions.

As a general rule, compositions containing 0.5 to 5,000 ppm of active substance are suitable; these values are recommended for the compositions which are ready for application. Ppm means "parts per million". The range from 0.5 to 5,000 ppm corresponds to a range of $5 \times 10^{-5}$ to 0.5% (percentages by weight).

Insofar as the compositions adapted to storage and to transport are concerned, these more advantageously contain from 0.5 to 95% (by weight) of active substance.

Thus, the compositions for agricultural use according to the invention may therefore contain the active substances according to the invention within very wide limits, ranging from $5 \times 10^{-5}$% to 95% (by weight).

According to what has already been stated, the compounds according to the invention are generally combined with carriers and, if desired, with surface-active agents.

In the present description, the term "carrier" is used to denote a natural or synthetic, organic or inorganic substance with which the active substance is combined to facilitate its application to the plant, to seeds or to the soil. This carrier is therefore generally inert and it must be agriculturally acceptable, especially on the treated plant. The carrier may be solid (clays, natural or synthetic silicates, silica, resins, waxes, solid fertilizers, and the like) or liquid (water, alcohols, ketones, oil fractions, aromatic or paraffinic hydrocarbons, chlorinated hydrocarbons, liquefied gases, and the like).

The surface-active agent may be an emulsifying, dispersing or wetting agent of an ionic or nonionic type. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (especially alkylphenols or arylphenols), salts of esters of sulphosuccinic acids, taurine derivatives (especially alkyltaurates), and phosphoric esters of alcohols or of phenols polycondensed with ethylene oxide. The presence of at least one surface-active agent is generally indispensable when the active substance and/or the inert carrier are not soluble in water and when water is the vector agent in the application.

The compositions employed in the invention may be in quite diverse, solid or liquid forms.

As solid forms of compositions there may be mentioned powders for dusting (with a content of active substances which may be up to 100%) and granulates, especially those obtained by extrusion, by compacting, by impregnation of a granulated carrier, by granulation from a powder (the content of compound of formula (I) in these granulates being between 0.5 and 80% in these latter cases).

As forms of compositions which are liquid or intended to constitute liquid compositions during the application, there may be mentioned solutions, in particular water-soluble concentrates, emulsifiable concentrates, emulsions, flowables, aerosols, wettable powders (or spraying powder), granulates and pastes.

Emulsifiable or soluble concentrates in most cases contain 10 to 80% of active substance, while emulsions or solutions which are ready for application contain, for their part, 0.001 to 20% of active substance. In addition to the active substance and the solvent, emulsifiable concentrates may, when necessary, contain a suitable cosolvent and from 2 to 20% of suitable additives such as stabilizers, surface-active agents, particularly emulsifiers, penetrating agents, corrosion inhibitors, colorants and adhesives.

Emulsions of any desired concentration, which are particularly suitable for the application to crops may be obtained from these concentrates by dilution with water.

Flowables, which can also be applied by spraying, are prepared so as to obtain a stable fluid product which does not settle and usually contain from 10 to 75% of active substance, from 0.5 to 15% of surface-active agents, from 0.1 to 10% of thixotropic agents, from 0 to 10% of suitable additives such as antifoams, corrosion inhibitors, stabilizers, penetrating agents and adhesives and, as carrier, water or an organic liquid in which the active substance is poorly soluble or insoluble; certain organic solid substances or inorganic salts may be dissolved in the carrier to help prevent sedimentation, or as antifreezes for water.

By way of example, here is the composition of a number of aqueous suspensions according to the invention:

EXAMPLE AS1

An aqueous suspension comprising the following is prepared:

| | |
|---|---|
| active substance (compound No. 4) | 500 g/l |
| wetting agent (ethylene oxide polycondensate with $C_{13}$ synthetic alcohol) | 10 g/l |
| dispersing agent (polyarylphenol phosphate condensed with ethylene oxide and converted into salt) | 50 g/l |
| antifreeze (propylene glycol) | 100 g/l |
| thickener (polysaccharide) | 1.6 g/l |
| biocide (sodium 4-methylhydroxybenzoate) | 3.3 g/l |
| water q.s. | 1 liter. |

EXAMPLE AS2

Aqueous Suspension

An aqueous suspension comprising the following is prepared:

| | |
|---|---|
| active substance (compound No. 7) | 100 g/l |
| wetting agent (ethylene oxide alkylphenol polycondensate) | 5 g/l |
| dispersing agent (Na naphthalenesulphonate) | 10 g/l |
| antifreeze (propylene glycol) | 100 g/l |
| thickener (polysaccharide) | 3 g/l |
| biocide (formaldehyde) | 1 g/l |
| water q.s. | 1 liter |

EXAMPLE AS3

Aqueous Suspension

An aqueous suspension comprising the following is prepared:

| | |
|---|---|
| active substance (compound No. 9) | 250 g/l |
| wetting agent (ethylene oxide polycondensate with $C_{13}$ synthetic alcohol) | 10 g/l |
| dispersing agent (sodium lignosulphonate) | 15 g/l |
| antigel (urea) | 50 g/l |
| thickener (polysaccharide) | 2.5 g/l |
| biocide (formaldehyde) | 1 g/l |
| water q.s. | 1 liter |

The wettable powders (or spraying powder) are usually prepared so that they contain 10 to 95% of active substance, and, in addition to the solid carrier, they usually contain from 0 to 5% of a wetting agent, from 3 to 10% of a dispersing agent and, when necessary, from 0 to 10% of one or more stabilizers and/or other additives such as penetrating agents, adhesives, or anticaking agents, colorants, and the like.

By way of example, here is the composition of a number of wettable powders.

EXAMPLE WP1

10% Strength Wettable Powder

| Example WP1: 10% strength wettable powder | |
|---|---|
| active substance (compound No. 4) | 10% |
| $C_{13}$ synthetic oxo alcohol of a branched type, condensed with ethylene oxide (8 to 10) (wetting agent) | 0.75% |
| neutral calcium lignosulphonate (dispersing agent) | 12% |
| calcium carbonate (inert filler) q.s. | 100% |
| Example WP2: 75% strength wettable powder containing the same ingredients as in the preceding example, in the proportions given below: | |
| active substance (compound No. 7) | 75% |
| wetting agent | 1.50% |
| dispersing agent | 8% |
| calcium carbonate (inert filler) q.s. | 100% |
| Example WP3: 90% strength wettable powder | |
| active substance (compound No. 9) | 90% |
| fatty alcohol - ethylene oxide condensate (wetting agent) | 4% |
| styrylphenol - ethylene oxide condensate (dispersing agent) | 6% |

-continued

| Example WP4: 50% strength wettable powder | |
|---|---|
| active substance (compound No. 4 according to the invention) | 50% |
| mixture of anionic and nonionic surfactants (wetting agent) | 2.5% |
| neutral sodium lignosulphonate (dispersing agent) | 5% |
| kaolin clay (inert carrier) | 42.5% |

To obtain these spraying powders or wettable powders, the active substance is mixed thoroughly with the additional substances in suitable mixers and is ground using mills or other suitable grinders. Spraying powders whose wettability and dispersion are advantageous are obtained thereby; they can be suspended in water at any desired concentration and this suspension can be employed very advantageously, in particular for the application to plant foliage.

The compounds of formula (I) may also be employed in the form of powders for dusting; a composition comprising 50 g of active substance and 950 g of talc can also be employed; it is also possible to employ a composition comprising 20 g of active substance, 10 g of finely divided silica and 970 g of talc; these constituents are mixed and ground and the mixture is applied by dusting.

The granulates for spreading are between 0.1 and 2 mm in size and can be manufactured by agglomeration or impregnation. In general, the granulates contain 0.5 to 25% of active substance and 0 to 10% of additives such as stabilizers, slow-release modifying agents, binders and solvents.

Here are two examples of a granulate composition:

EXAMPLES G 1 AND G2

| active substance 2 | 50 g | 200 g |
|---|---|---|
| propylene glycol | 50 g | 50 g |
| cetyl polyglycol ether | 2.5 g | 2.5 g |
| polyethylene glycol | 35 g | 35 g |
| kaolin (particle size: 0.3 to 0.8 mm) | 910 g | 760 g |

The compounds according to the invention can, furthermore, be formulated in the form of organic solutions encapsulated, particularly by interfacial polymerization, in capsules with polymeric walls based, for example, on polyamides of polyureas or on polyamide ureas. These capsules are in the form of concentrated aqueous dispersions which can be diluted at the time of use to obtain a spraying mixture.

The compounds according to the invention may be advantageously formulated in the form of water-dispersible granulates, also included within the scope of the invention.

These dispersible granulates, with an apparent density which is generally between 0.3 and 0.6, have a particle size which is generally between approximately 150 and 2,000, and preferably between 300 and 1,500 microns.

The active substance (compound No. 4) content of these granulates is generally between approximately 1% and 90%, and preferably between 25% and 90%.

The remainder of the granulate is essentially made up of a solid filler and, if desired, surface-active adjuvants endowing the granulate with water-dispersibility properties. These granulates can be essentially of two distinct types depending on whether the filler they contain is water-soluble or not. When the filler is water-soluble, it can be inorganic and, preferably, organic. Excellent results have been obtained with urea. In the case of an insoluble filler, the latter is preferably inorganic such as, for example, kaolin or bentonite. It is then accompanied by surface-active agents (in a proportion of 2 to 20% by weight of the granulate), more than half of these surface-active adjuvants consisting of at least one dispersing agent, essentially anionic, such as a poly(alkali metal or alkaline-earth metal naphthalenesulphonate) or an alkali metal or alkaline-earth metal lignosulphonate, the remainder consisting of nonionic or anionic wetting agents such as an alkali metal or alkaline-earth metal alkylnaphthalenesulphonate.

Furthermore, other adjuvants, such as antifoam agents, may be added, although this is not indispensable.

The granulate according to the invention may be prepared by mixing the necessary ingredients, followed by granulation according to a number of techniques which are known per se (pelletizer, fluid bed, sprayer, extrusion, and the like). The finishing operation is generally crushing followed by screening to the particle size chosen within the limits referred to above.

It is preferably obtained by extrusion, the operation being carried out as indicated in the examples below.

EXAMPLE DG1

Dispersible Granules Containing 90% of Active Substance

90% by weight of active substance (compound No. 7) and 10% of pearled urea are mixed in a mixer. The mixture is then ground in a toothed-roll crusher. A powder is obtained, which is moistened with approximately 8% by weight of water. The moist powder is extruded in a perforated-roll extruder. A granulate is obtained, which is dried and then crushed and screened so as to retain only the granules of a size between 150 and 2,000 microns respectively.

EXAMPLE DG2

Dispersible Granules Containing 75% of Active Substance

The following constituents are mixed in a mixer:

| active substance (compound No. 9) | 75% |
|---|---|
| wetting agent (sodium alkylnaphthalene-sulphonate) | 2% |
| dispersing agent (sodium polynaphthalene-sulphonate) | 8% |
| water-insoluble inert filler (kaolin) | 15% |

This mixture is granulated in a fluid bed, in the presence of water, and is then dried, crushed and screened so as to obtain granules of size between 0.16 and 0.40 mm.

These granules may be employed by themselves, in solution or dispersion in water, so as to obtain the required dosage. They may also be employed to prepare combinations with other active substances, especially fungicides, the latter being in the form of wettable powders or of granulates or aqueous suspensions.

As already stated, the aqueous dispersions and emulsions, for example compositions obtained by diluting with water a wettable powder or an emulsifiable concentrate according to the invention, are included within the general scope of the compositions which can be employed in the present invention. The emulsions may be of the water-in-oil or oil-in-water type and may have a thick consistency such as that of a mayonnaise.

The invention relates, moreover, to a process for treating plants and especially rice and other cereals against the diseases caused by phytopathogenic fungi belonging to the most diverse groups and especially on Pyricularia oryzae which are sensitive or resistant to various fungicides, especially to kasugamycin and to iprobenfos.

The feature of this process is that it consists in applying to these plants or to the place where they are cultivated an effective quantity of a composition containing a compound according to formula (I) as active substance. An "effective quantity" means a quantity sufficient to permit the control and the destruction of the fungi present on these plants. Nevertheless, the use dosages may vary within wide limits depending on the fungus to be combated, the type of crop, the climatic conditions and depending on the compound employed.

Plants means plants or parts of plants (foliage, roots, seeds and the like).

In practice, dosages ranging from 1 g/hl to 500 g/hl, corresponding substantially to dosages of active substance per hectare approximately from 10 g/ha to 20,000 g/ha give generally good results.

We claim:

1. A derivative of formula:

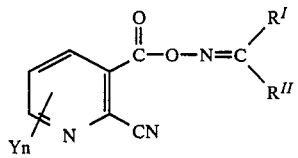

in which
- $R^I$ or $R^{II}$ which are identical or different, are a hydrogen atom, a linear or branched alkyl radical having from 1 to 18 carbon atoms;
or form, with the carbon atom bonded to the nitrogen atom, a 5- or 6-membered ring, itself capable of carrying a phenyl radical, through the intermediacy of two adjacent carbon atoms; a phenyl radical unsubstituted or substituted by a substituent chosen from the group consisting of a halogen atom, an alkyl having from 1 to 4 carbon atoms, an alkoxy having from 1 to 4 carbon atoms, an amino unsubstituted or substituted by an alkyl having 1 to 4 carbon atoms, a nitro, another dioxyalkylene ($C_1$–$C_3$) carried by two adjacent phenyl carbon atoms, a pyridyl radical;
- Y is a hydrogen or halogen atom, or an alkyl or alkoxy radical having from 1 to 4 carbon atoms; and
- n is an integer from 1 to 3.

2. The compound according to claim 1, in whose formula $R^1$ and $R^2$, which are identical or different, are a hydrogen atom, an alkyl having from 1 to 4 carbon atoms or a phenyl, unsubstituted or substituted.

3. A fungicidal composition which comprises an effective fungicidal amount of a compound according to claims 1 or 2.

4. A method for combating the fungal diseases of plants, wherein an effective fungicidal amount of a compound according to claims 1 or 2 is applied to these plants or to the place where they are cultivated.

* * * * *